(12) United States Patent
Boiten

(10) Patent No.: US 9,775,715 B2
(45) Date of Patent: Oct. 3, 2017

(54) PROSTHETIC KNEE JOINT WITH INCORPORATED VACUUM PUMP

(75) Inventor: Herman Boiten, Göttingen (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days.

(21) Appl. No.: 13/811,216

(22) PCT Filed: Jul. 21, 2011

(86) PCT No.: PCT/EP2011/003658
§ 371 (c)(1),
(2), (4) Date: Jan. 18, 2013

(87) PCT Pub. No.: WO2012/010309
PCT Pub. Date: Jan. 26, 2012

(65) Prior Publication Data
US 2013/0123941 A1    May 16, 2013

(30) Foreign Application Priority Data
Jul. 21, 2010 (DE) .................. 10 2010 031 723

(51) Int. Cl.
| A61F 2/38 | (2006.01) |
| A61F 2/64 | (2006.01) |
| A61F 2/74 | (2006.01) |
| A61F 2/68 | (2006.01) |
| F04B 33/00 | (2006.01) |

(Continued)

(52) U.S. Cl.
CPC .............. *A61F 2/38* (2013.01); *A61F 2/644* (2013.01); *A61F 2/68* (2013.01); *F04B 33/00* (2013.01); *A61F 2002/5006* (2013.01); *A61F 2002/742* (2013.01); *A61F 2002/747* (2013.01); *A61F 2002/802* (2013.01)

(58) Field of Classification Search
CPC ...... A61F 2/64; A61F 2/68; A61F 2/78; A61F 2/80; A61F 2/642; A61F 2/644; A61F 2/646; A61F 2002/742; A61F 2002/802; A61F 2002/807
USPC ................ 623/24–26, 32, 34, 39–46, 47–55
See application file for complete search history.

(56) References Cited

U.S. PATENT DOCUMENTS

| 5,545,233 A | 8/1996 | Fitzlaff |
| 6,117,177 A | 9/2000 | Chen et al. |

(Continued)

FOREIGN PATENT DOCUMENTS

| DE | 4233247 A1 | 4/1994 |
| DE | 29905842 U1 | 12/1999 |

(Continued)

OTHER PUBLICATIONS

3R60-PRO Hydraulic Knee. Sep. 2009. The O&P Edge.*

(Continued)

*Primary Examiner* — Thomas J Sweet
*Assistant Examiner* — Christie Bahena
(74) *Attorney, Agent, or Firm* — Holland & Hart LLP

(57) ABSTRACT

The invention relates to prosthetic knee joint comprising an upper part, which has an upper connecting means, and a lower part, which is pivotably mounted on the upper part and which has a lower connecting means. A vacuum pump with an inlet and an outlet, said pump being driven by the relative movement of the upper part to the lower part, is associated with the prosthetic knee joint.

17 Claims, 13 Drawing Sheets

(51) Int. Cl.
    *A61F 2/50* (2006.01)
    *A61F 2/80* (2006.01)

(56) References Cited

U.S. PATENT DOCUMENTS

| | | | |
|---|---|---|---|
| 6,554,868 B1 | 4/2003 | Caspers | |
| 6,645,253 B2 * | 11/2003 | Caspers | 623/26 |
| 6,761,742 B2 | 7/2004 | Caspers | |
| 2003/0191539 A1 * | 10/2003 | Caspers | A61F 2/7812 623/35 |
| 2005/0240282 A1 * | 10/2005 | Rush et al. | 623/26 |
| 2006/0212130 A1 * | 9/2006 | Collier | 623/26 |
| 2007/0196222 A1 * | 8/2007 | Mosler et al. | 417/472 |
| 2008/0269912 A1 * | 10/2008 | Gobbers | A61F 2/60 623/27 |
| 2009/0036998 A1 * | 2/2009 | Finlinson et al. | 623/34 |
| 2009/0157196 A1 * | 6/2009 | Danzig et al. | 623/34 |
| 2009/0281637 A1 * | 11/2009 | Martin | 623/34 |
| 2010/0312360 A1 * | 12/2010 | Caspers | 623/34 |
| 2012/0123559 A1 | 5/2012 | Mosler et al. | |

FOREIGN PATENT DOCUMENTS

| | | |
|---|---|---|
| DE | 102004036669 A1 | 3/2006 |
| DE | 60115216 T2 | 8/2006 |
| DE | 60126154 T2 | 10/2007 |
| DE | 202009012627 U1 | 1/2010 |
| RU | 2055548 C1 | 3/1996 |
| RU | 40584 U1 | 9/2004 |

OTHER PUBLICATIONS

Derwent abstract of JP2007-252450. Nakaya, Okuda. Mar. 22, 2006.*
PCT International Search Report for PCT International Patent Application No. PCT/EP2011/003658, dated Oct. 5, 2011.

\* cited by examiner

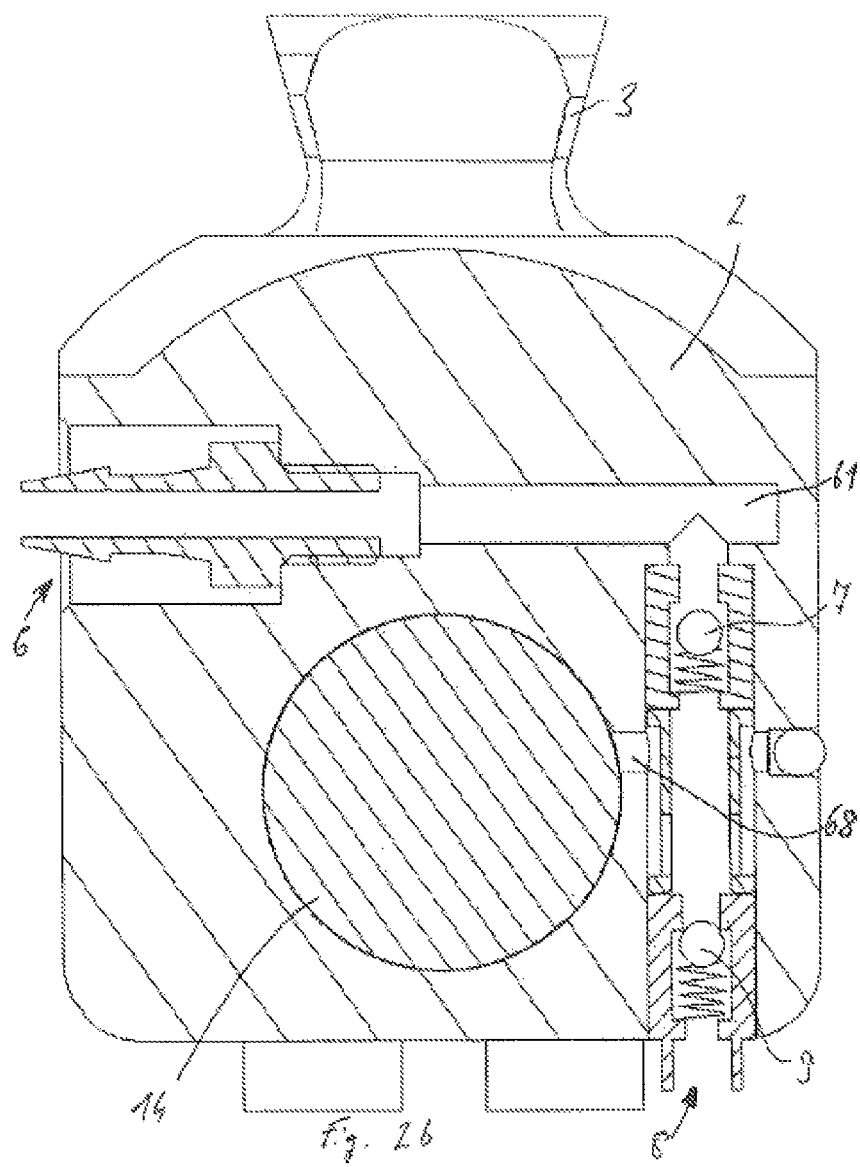

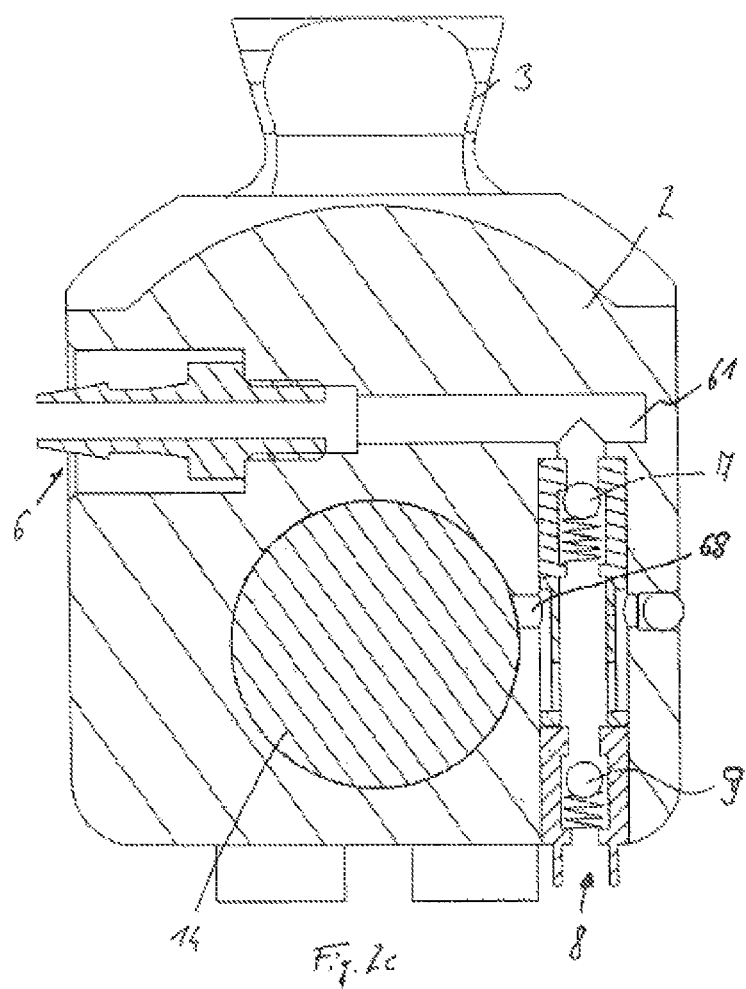

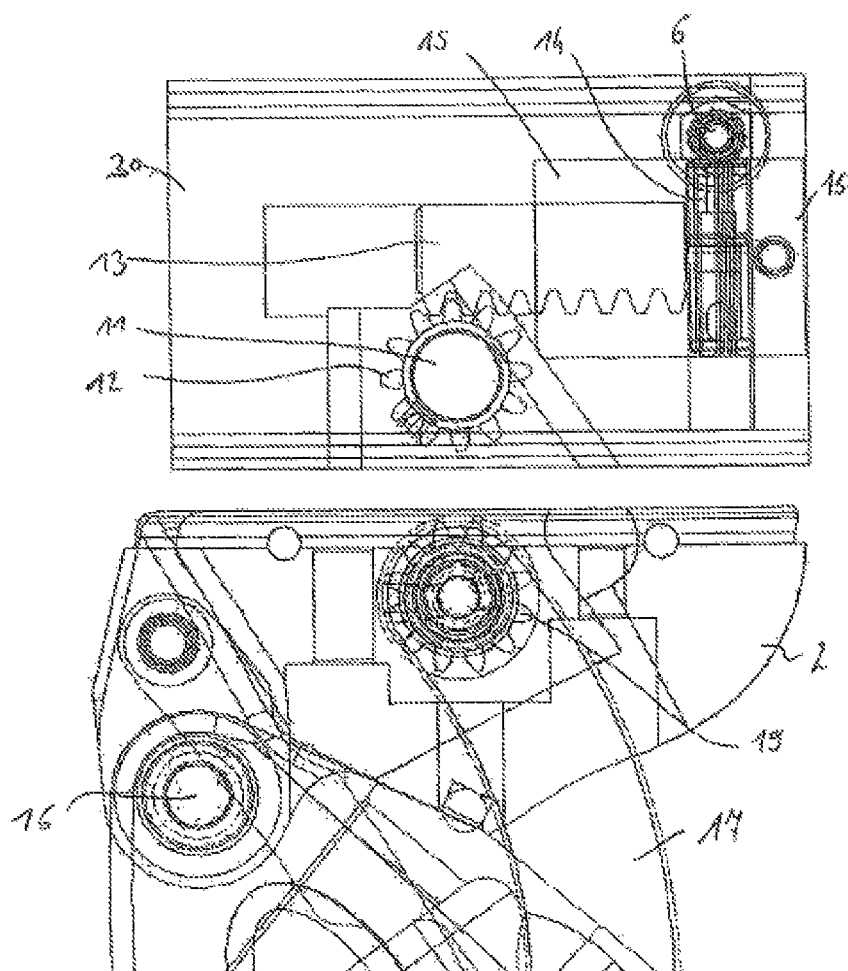

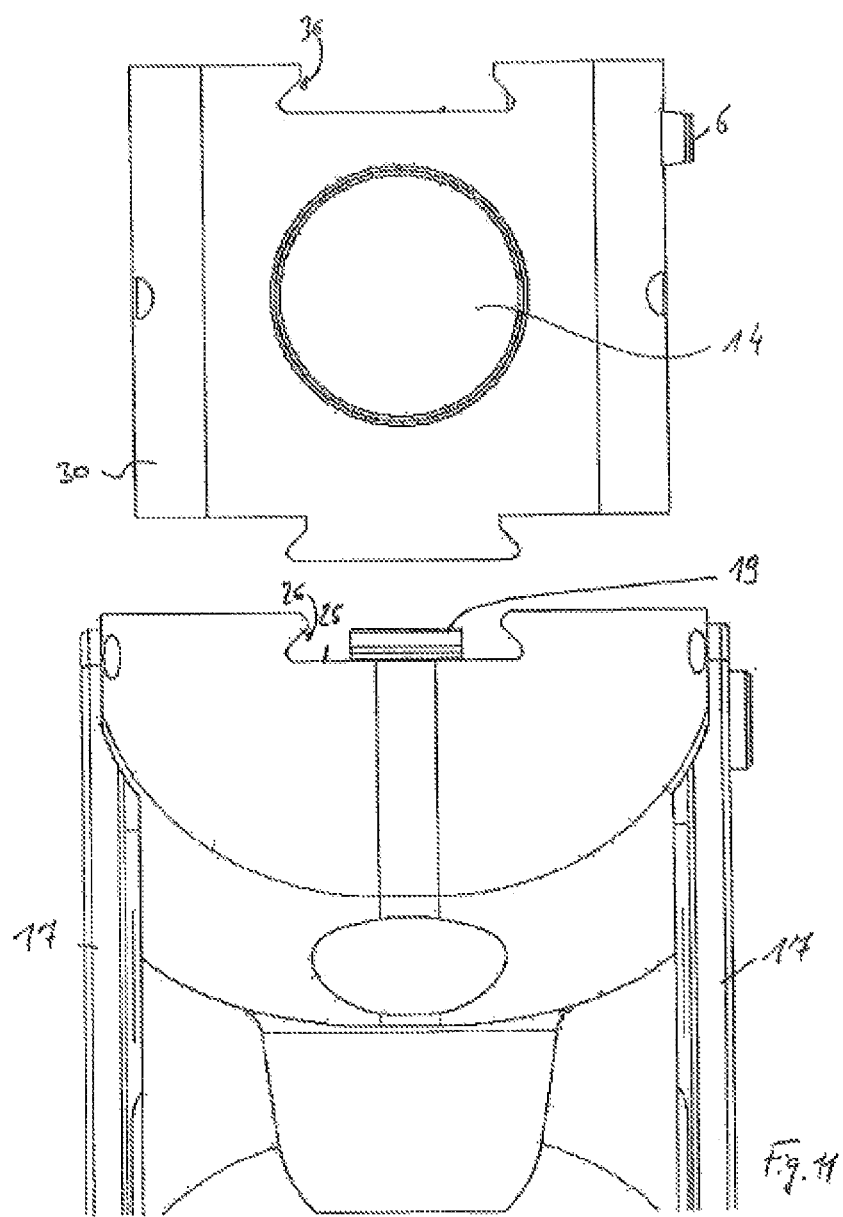

PROSTHETIC KNEE JOINT WITH INCORPORATED VACUUM PUMP

The invention relates to a prosthetic knee joint with an upper part, which has upper connecting means, and with a lower part, which is mounted pivotably on the upper part and has lower connecting means. The upper and lower connecting means serve to secure the prosthetic knee joint on distally and proximally adjoining components. The lower connecting means generally serve for securing to a below-knee device, on which a prosthetic foot is secured in turn. The one or more upper connecting means generally serve for the securing of a thigh socket, which serves to receive a thigh stump.

To give a prosthesis wearer sufficient security when wearing the prosthesis, it is necessary for the prosthesis to be arranged safely and firmly on the stump. Fastenings using straps, loops and buckles have the disadvantage that the stump can become constricted, and that variations in the volume of the stump during walking cannot be taken into account. It has thus proven expedient to use so-called suction sockets, which generally consist of a soft, airtight inner socket, which is arranged or secured on a dimensionally stable outer socket. Connecting devices for securing the prosthetic knee joint are located on the outer socket, i.e. seats for an upper connecting means. The inner socket or liner lies over the full surface of the thigh stump and is substantially airtight with the outer socket. The space between the liner and the outer socket is evacuated to create a negative pressure condition, such that fixing of the liner on the outer socket is achieved by the negative pressure condition (e.g., underpressure). Through the adherence of the liner on the thigh stump, stable coupling is thus achieved between the prosthetic knee joint and the stump.

DE 10 2004 036 669 A1 describes a pump with at least one flexible wall of an enclosed fluid volume, which wall can be deformed by means of a first force in a direction resulting in a decrease in volume and, after a preceding decrease in volume, can be deformed by means of a second force in a direction resulting in an increase in volume. The pump has an inlet valve with an inlet line and an outlet valve with an outlet line of the fluid volume. An elastic material, placed flat on the flexible wall, is compressed upon a deformation of the flexible wall by one of the forces, and the restoring force of the elastic material moves the wall back after the effect of the force ceases. The pump can be used as a vacuum pump that generates a vacuum as a result of the body weight when the foot is put down. The field of use mentioned is that of vacuum support of a suction socket.

DE 601 26 154 T2 describes a vacuum pump in a shock absorber, which vacuum pump is activated based on weight.

Weight-based vacuum pumps often have a short adjustment travel, since an axial shift during walking or standing is only desired or admissible to a limited extent in order to avoid sinking of the body during walking. Coupling the vacuum pump to a shock absorber can lead to difficulties in controlling the swing phase.

The object of the present invention is to make available a prosthetic knee joint that has improved means for securing on a thigh stump.

According to the invention, this object is achieved by a prosthetic knee joint having the features of the main claim. Advantageous embodiments and developments of the invention are set out in the dependent claims, the description and the figures.

The prosthetic knee joint according to the invention, with an upper part, which has upper connecting means, and with a lower part, which is mounted pivotably on the upper part and has lower connecting means, is characterized in that a vacuum pump with an inlet and an outlet is assigned to the prosthetic knee joint and is driven by the relative movement of the upper part and the lower part. By means of the relative movement of the upper part with respect to the lower part, i.e. a rotation movement, being transferred to the vacuum pump, it is possible to make available a relatively long adjustment travel, such that a large volume can be moved in the vacuum pump. In addition, during the movement, considerable forces act in the knee joint, which forces can easily be used to generate the vacuum. It is thereby also possible to exploit a considerable step-up of the relative movement between the upper part and the lower part via a gear, such that, even at small flexion or extension angles, it is possible to achieve a considerable shift and a long adjustment travel of the vacuum pump.

The vacuum pump can be designed such that an underpressure is generated during flexion and an expulsion from the pump chamber occurs during extension. Greater forces generally act during flexion, such that the flexion movement is better suited than the extension movement for generating a vacuum.

A suction piston is advantageously arranged in the vacuum pump and is moved as a result of the relative movement between the upper part and the lower part inside the pump cylinder or in the piston chamber. The suction piston can be designed as an oscillating piston or linear piston. In an embodiment as a linear piston, the rotation movement is converted into a linear movement, and, when an oscillating piston is used, the rotation movement of the upper part with respect to the lower part can be retained. A force-transferring device is preferably arranged between the upper part and the lower part such that the relative movement of the lower part with respect to the upper part can be transferred to the vacuum pump. If appropriate, a transmission mechanism can be provided by a toothed wheel gear or by a lever gear, such that an increase in force or travel can be achieved. It is likewise possible that a toothed wheel or several toothed wheels are provided for force transfer, such that a toothed wheel gear or a toothed wheel/lever gear can be used to drive the pump. The prosthetic knee joint can be designed as a monocentric or polycentric prosthetic knee joint. In both embodiments, a vacuum pump can be used that is driven by the relative movement of the upper part with respect to the lower part.

A check valve is provided which prevents a backflow of air into a suction line or into a suction space, such that air pumped out of the space between liner and outer socket cannot flow back into the space. The underpressure is maintained in this way. An outlet line can likewise be provided with a check valve, such that the vacuum pump can at all times suck air from the space provided therefor between liner and outer socket. In order to attenuate expulsion noises, a damper is arranged in front of the outlet or in the outlet.

In one variant of the invention, the vacuum pump is integrated directly in the upper part or the lower part, such that the generally solid components of the upper part and of the lower part are additionally used by means of a relatively compact structure in the form of the vacuum pump being installed. It is thereby possible to integrate a further functional element without reducing the structural strength of the upper part or of the lower part. If the vacuum pump is integrated in the upper part, this has the advantage that a direct connection between the outer socket and the vacuum pump can be produced without having to provide a complex hose system. The connection between the space to be evacuated and the vacuum pump can be made rigid, since no relative movement takes place between the outer socket and the vacuum pump. If it is more sensible, for design reasons, to accommodate the vacuum pump in the lower part, a suction line must be provided from the lower part to the outer socket.

In one variant, provision is made that the vacuum pump is secured on the upper part or lower part as a separate component. For example, the vacuum pump can be provided as an adapter device which is secured on the upper part. The adapter then has upper connecting means, for example a securing pylon. It is thereby possible to equip a prosthetic knee joint optionally with or without a vacuum pump such that, with otherwise the same design of the prosthetic knee joint, only a module has to be removed or added in order to permit adjustment to a desired socket design. However, the vacuum pump can be provided in any desired arrangement and embodiment, so long as it is driven by the relative movement of the upper part with respect to the lower part. In particular, it can be arranged in front of or behind the upper or lower part, can connect upper part and lower part to each other, or can itself form the joint. In particular, it can also be connected to a part of the force-transferring device or form a part of this force-transferring device.

Illustrative embodiments of the invention are explained in more detail below with reference to the figures, in which:

FIG. 2b shows a variant of FIG. 2a during evacuation;

FIG. 2c shows a variant of FIG. 2a during expulsion;

FIG. 10 shows a sectional view of a detail;

FIG. 11 shows a rear view of a detail.

Figure 1:
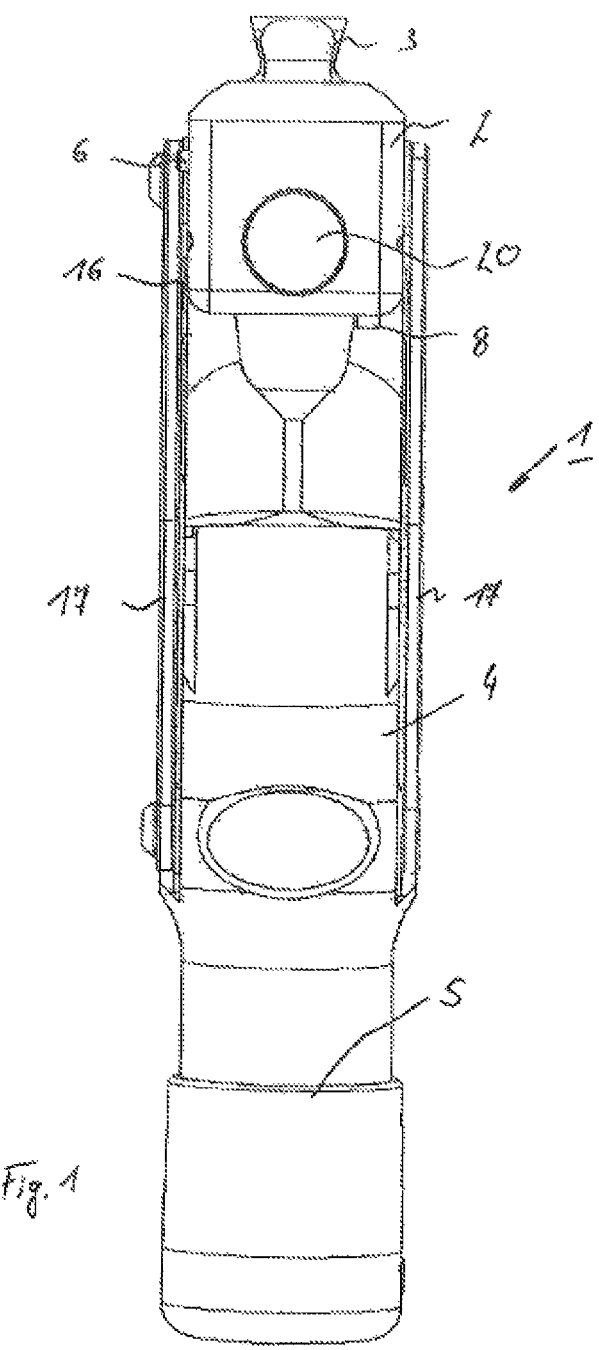
FIG. 1 shows a front view of a prosthetic knee joint.

A prosthetic knee joint 1 is shown in a front view in FIG. 1, with an upper part 2 that has upper connecting means 3 in the form of a securing pylon. The upper connecting means 3 serve to secure the upper part 2, and therefore the entire prosthetic knee joint 1, to a thigh socket (not shown) via which the prosthetic knee joint 1 is fitted to the body of the prosthesis user. The thigh socket generally serves to receive the thigh stump; other securing possibilities can likewise be provided. Generally, the thigh socket provides a substantially closed sleeve which is open at the top and into which the stump is inserted. Before the insertion of the stump, a so-called liner, generally a silicone liner, is pulled over the stump. The liner is then inserted into the outer socket and turned over at the upper edge of the outer socket, such that a substantially airtight chamber is created between the outside of the liner and the inside of the outer socket. By applying an underpressure, it is possible to act on or improve the fixing of the liner and, therefore, of the thigh stump in the outer socket.

The upper part 2 is mounted in an articulated manner relative to a lower part 4. Lower connecting means 5 are provided on the lower part 4, for example for securing a below-knee device and a prosthetic foot. Damping devices, drives and/or control devices can likewise be provided in the lower part 4 in order to influence the relative movement between the upper part 2 and lower part 4. The lower part 4 can be mounted pivotably relative to the lower part 4 via a single pivot axis 16. Alternatively, in a polycentric knee joint, a combined pivoting movement with migrating instantaneous poles can be formed, such that the pivoting movement of the upper part 2 relative to the lower part 4 is defined not about a fixed pivot axis arranged on the lower part 4, but instead by an instantaneous pivot axis that changes position.

Levers 17, of which the function is explained in more detail below, are arranged to the sides of the upper part 2 and the lower part 4.

A lateral suction-air attachment 6 and a downwardly oriented outlet 8 are provided on the upper part 2. The suction-air attachment 6 serves for attaching a vacuum pump 20, which is integrated in the upper part 2 in the illustrative embodiment shown, to a suction socket. The outlet 8 serves to allow compressed air to leave the cylinder of the vacuum pump 20 during a return movement of a suction piston.

Figure 2A:
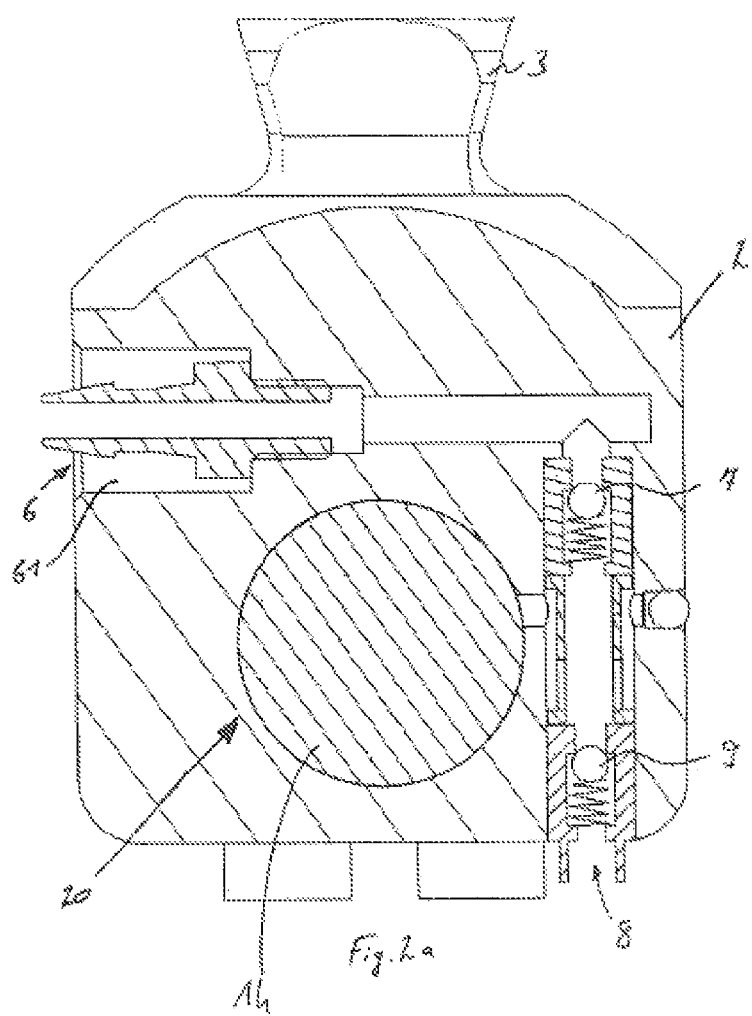
FIG. 2a shows a sectional view of an upper part in a frontal plane.

The upper part 2 is shown in a sectional view in FIG. 2a. The section runs through the frontal plane of the upper part 2. An upper connecting means 3 in the form of a securing pylon is either screwed onto the upper part 2 or is formed in one piece with the latter. The suction-air attachment 6 and the outlet 8 are also inserted in the upper part 2. The suction-air attachment 6 is screwed into a bore 61. The bore 61 serves as a channel through which the air suctioned from the thigh socket (not shown) is conveyed to the vacuum pump 20 via a branch line 68. The suction piston 14 of the vacuum pump 20 can be seen, which suction piston 14 executes a reciprocating movement inside the upper part 2, in order to execute a forward and backward movement during the flexion or extension. From the bore 61, the suction air is conveyed through a check valve 7 to the suction piston 14. In a return movement of the suction piston 14, the check valve 7 prevents a backflow of the compressed air into the suction socket. So as not to block the rearward movement of the suction piston 14, a check valve 9 is provided upstream of the outlet 8 through which the compressed air can flow out.

FIG. 2b shows the valve position during the suctioning of air: the upper check valve 7 is opened, such that air can flow from the suction-air attachment 6 through the bore 61 into the suction chamber. The check valve 9 prevents ambient air from flowing in through the outlet 8.

In FIG. 2c, the check valve 9 assigned to the outlet 8 is opened, and air compressed by the suction piston 14 can flow out into the environment.

Figure 3:
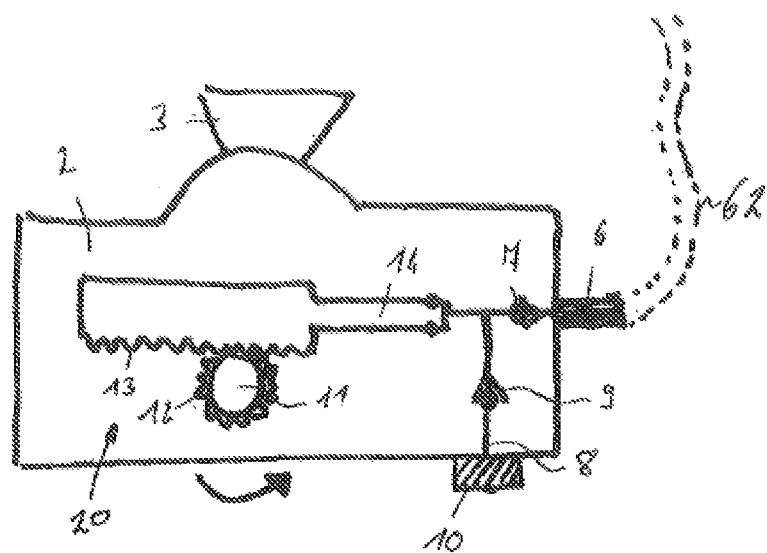
FIG. 3 shows a schematic view of the construction.

The schematic set-up of the pump 20 is shown in FIG. 3. On the upper part 2, a suction line 62 is arranged on the suction-air attachment 6 and leads to a suction-air attachment on a thigh socket (not shown). Check valves 7 and 9 for limiting the through-flow in the respective direction of flow are also shown. A sound damper 10 for damping the noise of the expelled air is arranged on the outside of the outlet 8. The damper 10 can likewise be arranged in the outlet 8. The vacuum pump 20 is arranged inside the upper part 2 and has a suction piston 14, which is connected to a toothed rack 13. The toothed rack 13 meshes with a toothed wheel 12, which is mounted on a shaft 11. During a flexion movement of the prosthetic knee joint and a shifting of the upper part 2 relative to the lower part 4, a relative movement of the toothed rack 13 with respect to the toothed wheel 12 causes a shifting of the suction piston 14, as a result of which an underpressure is generated, such that air is sucked through the suction line 62 and the suction-air attachment 6 into the space freed by the suction piston 14. The flexion movement, which is indicated by the arrow, leads to a shifting of the suction piston 14 to the left in FIG. 3. The relative movement can be effected by the shaft 11 remaining fixed in position in terms of rotation, while the upper part 2 rotates around the shaft 11.

Figure 4:
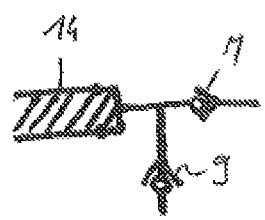
FIG. 4 shows a schematic view of the function principle during operation.
Figure 4:
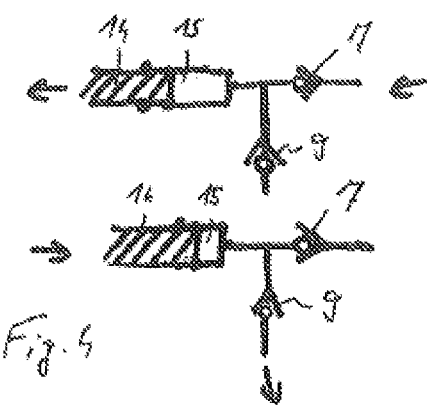

FIG. 4 shows three positions of the suction piston 14 that correlate with the position of the prosthetic knee joint. In the upper view, the suction piston 14 is pushed in fully. The prosthetic knee joint is located in the extended position. Both check valves 7, 9 are closed.

The middle view shows the prosthetic knee joint in a flexion movement, such that the suction piston 14 moves out of the cylinder 15 of the pump 20. In this way, a suction volume is freed, such that air from the socket can flow through the first check valve 7 into the cylinder 15. If an extension movement is initiated, such that the lower part 4 is moved forward, the suction piston 14 also shifts in the direction of the arrow and reduces the suction volume, and the air thereby compressed inside the cylinder 15 escapes through the check valve 9, 10 and out of the outlet 8.

Figure 5:
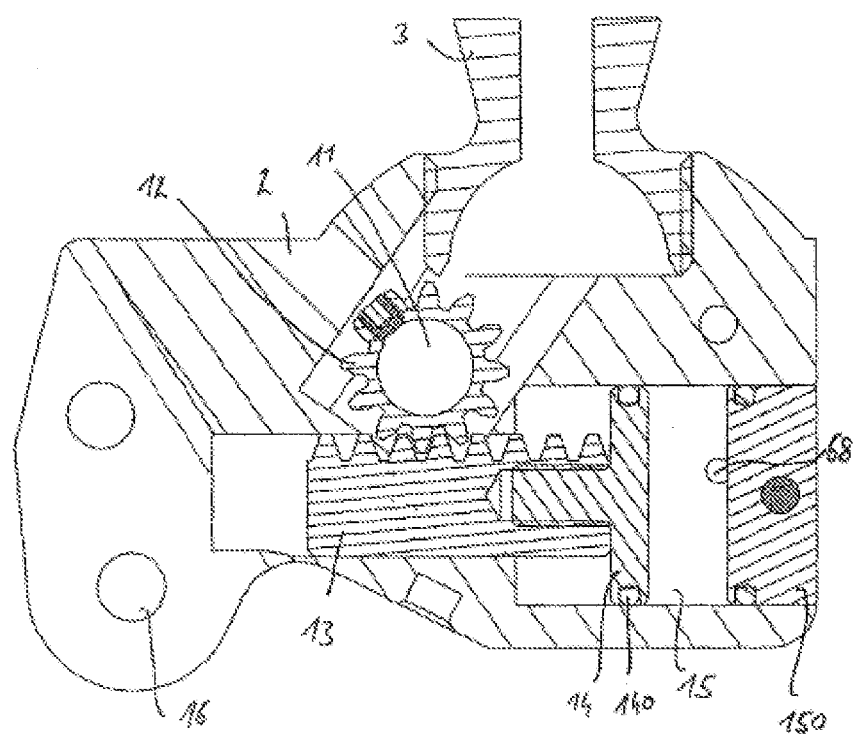
FIG. 5 shows a sectional view of the upper part in a sagittal plane.

FIG. 5 shows, in a sectional view in a sagittal plane, an upper part 2 with a screwed-in upper connecting means 3 in the form of an adapter. The upper part 2 is shown having a solid construction with cavities formed therein to receive various components, including pump components. Below the adapter, a toothed wheel 12 is mounted on a shaft 11. The shaft 11 is arranged pivotably inside the upper part 2 and is rotated relative to the upper part 2 via the levers 17, which are shown in FIG. 1, in the event of a pivoting movement of the upper part 2 about a pivot axis 16. This is achieved by the fact that the shaft 11 is mounted in a rotationally fixed manner on the levers 17.

A toothed rack 13, which meshes with the toothed wheel 12, is also arranged inside the upper part 2. The toothed rack 13 is assigned a suction piston 14. In the illustrative embodiment shown, the suction piston 14 is screwed into the toothed rack 13. The suction piston 14 is sealed off with respect to the cylinder 15 by a seal 140. A stopper 150 forms the closure of the suction chamber at the side lying opposite the suction piston 14. The branch channel 68 to the valve arrangement (not shown) opens into the suction chamber. The suction piston 14 is shown at a distance from the stopper 150. This means that a vacuum has been created in the cylinder 15 by the movement of the suction piston 14 away from the stopper 150, as a result of which air from the suction socket has been sucked through the suction-air attachment 6, the bore 61 and the branch channel 68. The toothed rack 13 and the suction piston 14 are not yet located at the maximum distance from the stopper 150, which in turn means that no maximum flexion of the prosthetic knee joint and a maximum shifting of the upper part relative to the lower part has taken place.

Figure 6:
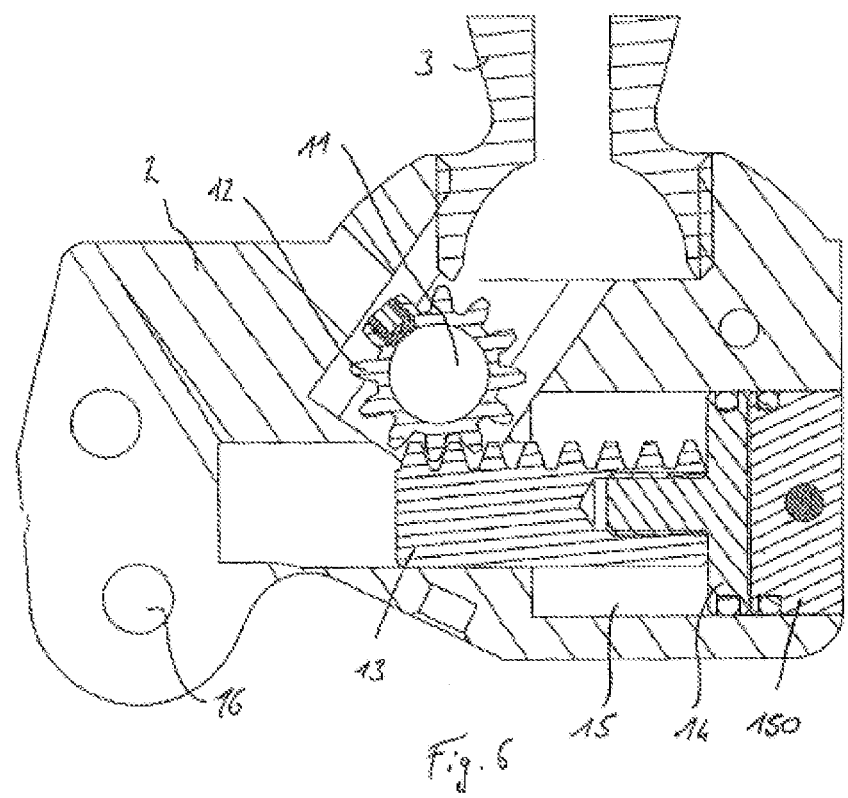
FIG. 6 shows a variant of FIG. 5 in a closed position.

In FIG. 6, the variant according to FIG. 5 is shown in a position of maximum extension. The suction piston 14 bears on the stopper 150. All the air from the cylinder 15 has been expelled through the branch line 68 and the check valve 8 (not shown).

Figure 7A:
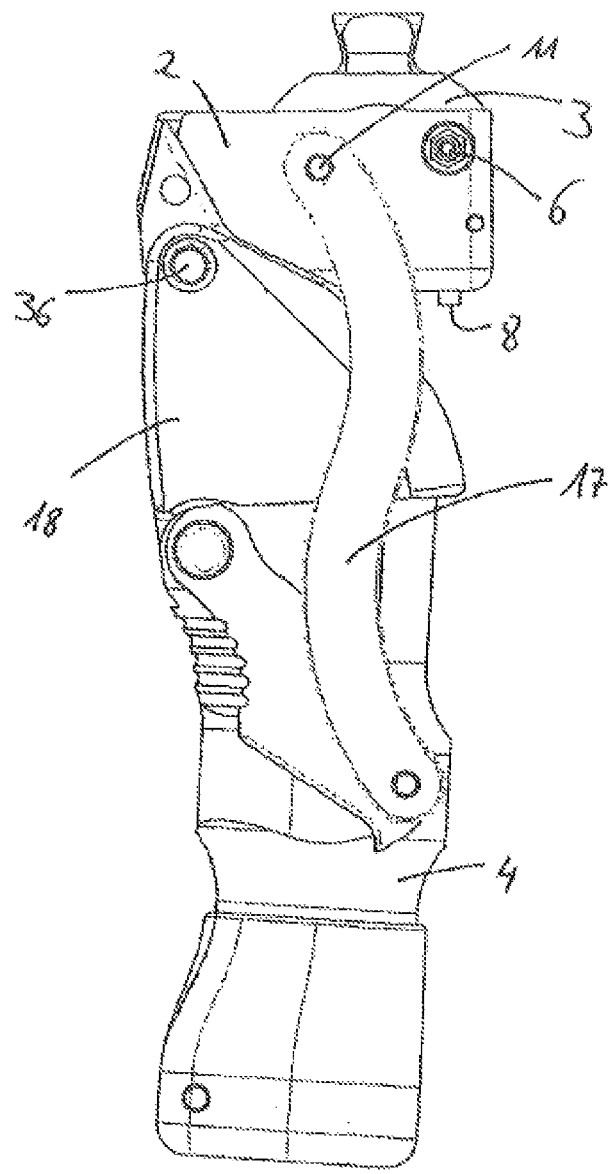
FIG. 7a shows a side view of a prosthetic knee joint according to FIG. 1 in an extension position.

FIG. 7*a* is the side view of a polycentric prosthetic knee joint in the position of extension. It shows the suction-air attachment 6, the outlet 8, and the securing of the lever 17, the so-called front link, on the shaft 11, on which the toothed wheel 12 of FIG. 6 is in turn placed. The lever 17 is connected in a rotationally fixed manner to the shaft 11 and, at its lower end, is pivotably mounted pivotably on the lower part 4. A second lever 18, the so-called rear link, is mounted thereon and is arranged on the upper part 2 via the axis 36. During a flexion of the upper part 2 relative to the lower part 4, the rotation movement of the upper part is converted into a rotation movement of the toothed wheel 12 relative to the upper part 2 and, therefore, to the toothed rack 13.

As an alternative to the rotary securing of the shaft 11 via the levers 17, it is possible, for example in a monocentric joint, that a stationary toothed wheel, which is arranged about a pivot axis, is coupled to the toothed rack 13 via a toothed wheel gear. It may likewise be possible to transfer the rotation movement not via a toothed rack 13 to an oscillating suction piston 14 for generating an underpressure, but instead directly or via a gear to an oscillating piston that executes a rotary movement in the upper part 2.

Figure 7B:
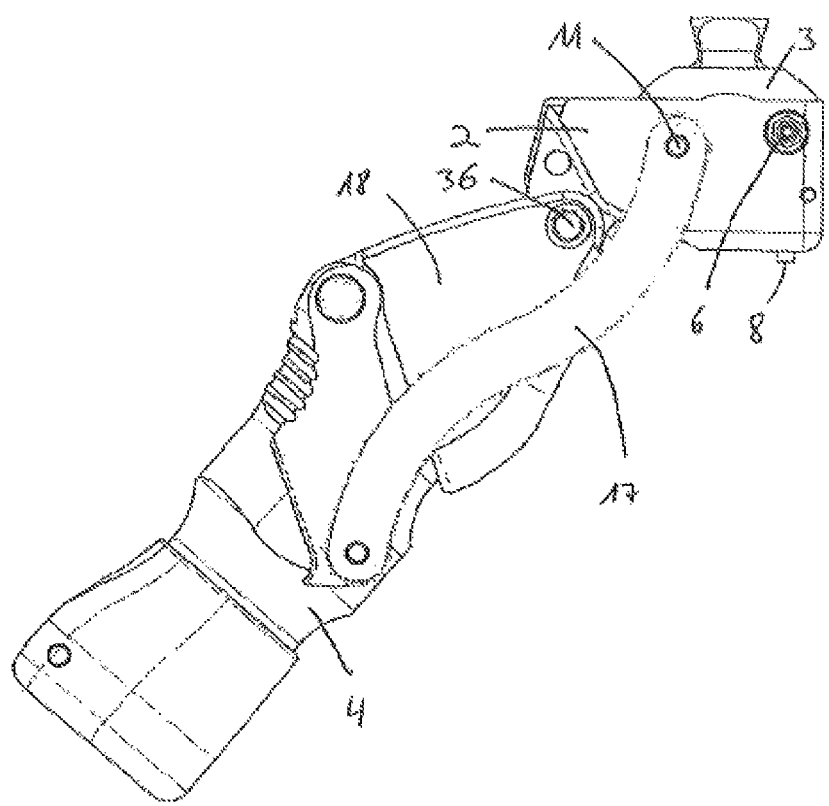
FIG. 7b shows a side view of a prosthetic knee joint according to FIG. 1 in a flexion position.

FIG. 7*b* shows the polycentric prosthetic knee joint from FIG. 7*a* in the position of flexion. The lower part 4 is rotated relative to the upper part 2, this relative movement having been transferred by the lever 17 via the shaft 11 to the toothed wheel 12 lying behind and, therefore, to the toothed rack 13. It can be clearly seen that upper part 2, lower part 4, rear link 18 and front link 17 have moved in relation to one another, and the axis of rotation of the knee joint is not formed by an independent component. It can thus be clearly seen from FIGS. 7*a* and 7*b* that this is a polycentric prosthetic knee joint.

Figure 8:
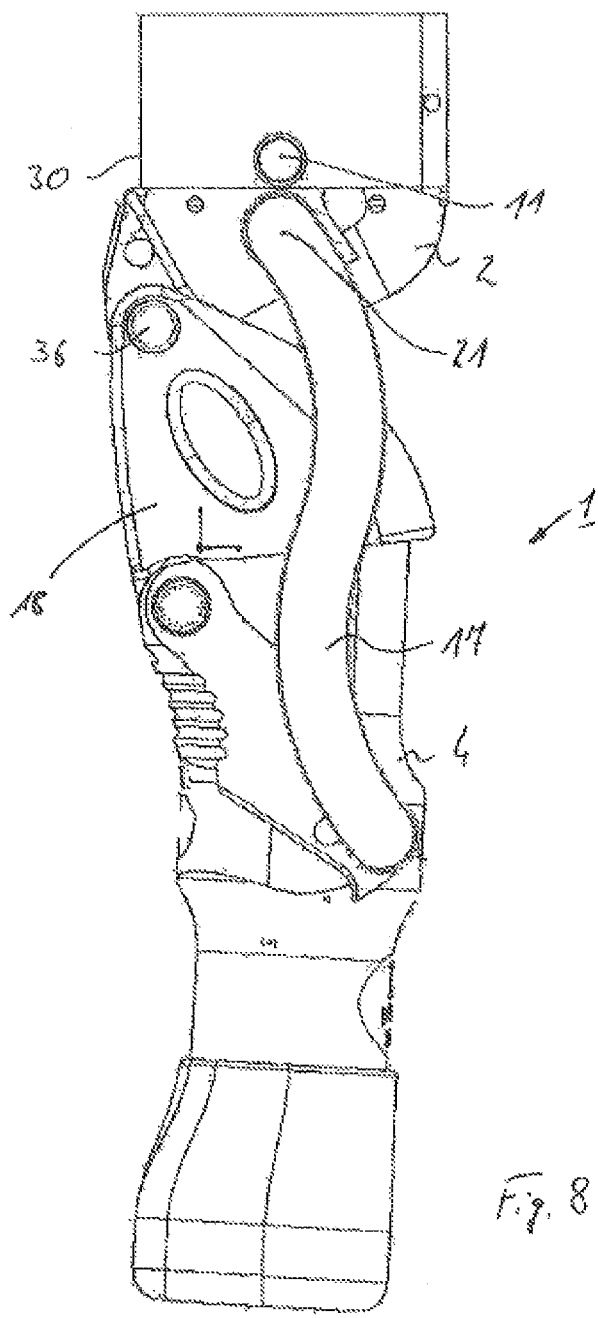
FIG. 8 shows a variant of a prosthetic knee joint in a side view.

FIG. 8 shows a variant of the polycentric prosthetic knee joint 1 from FIG. 7. Instead of the vacuum pump 20 being integrated in the upper part 2, provision is made that an add-on piece with a housing 30 is fitted onto the upper part 2. The pump mechanism is integrated in the housing 30. The drive is likewise effected by the relative movement of the upper part 2 with respect to the lower part 4. A shaft 21 connected to the lever 17 in the upper part 2 is equipped with a force-transferring device, with which the relative movement between the shaft, arranged in a rotationally rigid manner on the lever 17, and the upper part 2 is transferred to the drive shaft 11 of the pump device in the housing 30. In an alternative to the arrangement of the shaft 21 on the lever 17, the rotation movement can be transferred also by a toothed wheel gear arranged in the upper part 2.

Figure 9:
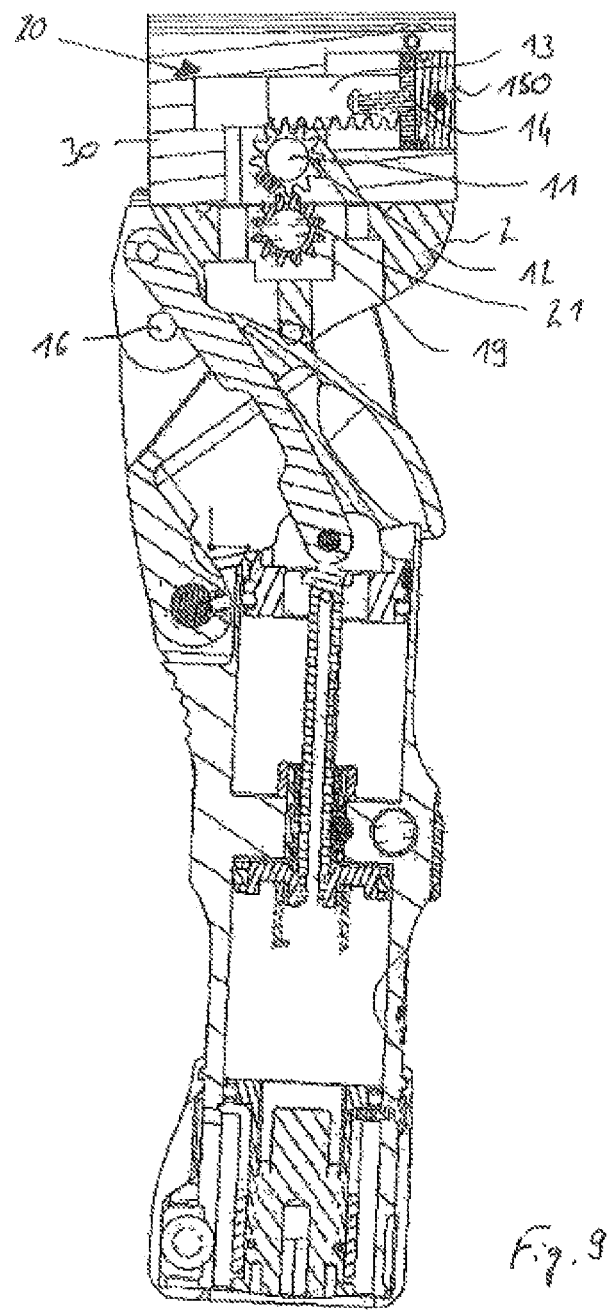
FIG. 9 shows a sectional view of FIG. 8 in a sagittal plane.

FIG. 9 shows the set-up of the prosthetic knee joint 1 in a sectional view in a sagittal plane. The shaft 21 is connected in a rotationally fixed manner to a toothed wheel 19 as force-transferring device. If the upper part 2 is shifted about the pivot axis 16, the upper part 2 rotates relative to the shaft 21 on account of the rotationally rigid fastening to the lever 17. This leads to a rotation movement that transfers to the toothed wheel 12 of the vacuum pump 20 in the housing 30. Here too, the rotation movement is transferred from the toothed wheel 12 to the suction piston 14 via the toothed rack 13. The upper connecting means are not shown and can be secured on the housing 30.

A detail view is shown in FIG. 10. The pivot axis 16, on which the upper part 2 is secured, can be seen, and also the toothed wheel 19 and the lever 17. The toothed wheel 19 in the upper part 2 is located inside a groove and protrudes from a bottom surface, such that the corresponding toothed wheel 12 of the pump 20 in the housing 30 can engage therewith in a form-fitting manner. The housing 30 can be pushed onto the upper part 2 and can be locked there. In this way, it is possible to design the pump as a module which, when required, can be fitted onto the upper part 2 or can be removed therefrom. Instead of the housing 30, an upper connecting means in the form of the adapter can be fitted onto the groove or the slide guide and can be locked there. On the upper face of the housing 30, a securing device is formed that corresponds to the configuration on the upper face of the upper part 2, such that an adapter without upper connecting means can be secured on the upper face of the housing 30. FIG. 10 likewise shows the cylinder 15, the suction piston 14, the suction-air attachment 6 and the stopper 150.

FIG. 11 shows the rear view of the embodiment according to FIG. 10. The toothed wheel 19 can be seen protruding above a bottom surface 25 in a dovetail guide 26. The figure likewise shows the corresponding dovetail guide on the upper face of the housing 30, in which an adapter can be inserted.

The invention claimed is:

1. A prosthetic knee joint, comprising:
an upper part having an upper connecting portion configured to connect the prosthetic knee joint to a proximal prosthetic member, the upper part having a solid construction;
a lower part mounted pivotably via a pivot axis on the upper part and having a lower connecting portion configured to connect the prosthetic knee joint to a distal prosthetic member;
a vacuum pump integrated into the upper part to provide a vacuum to a socket for holding a residual limb, the vacuum pump having an inlet and an outlet, the vacuum pump including a suction piston;
at least one piston bore formed in the upper part of the prosthetic knee joint, the suction piston being positioned in the at least one piston bore and operable to generate a vacuum upon relative pivotal movement of the upper part with respect to the lower part of the prosthetic knee joint;
a force transferring device arranged between the upper part and the lower part, the force-transferring device transferring relative movement of the lower part, with respect to the upper part, to the suction piston in the vacuum pump;
a suction line or suction space established in the upper part;
a first check valve arranged in the upper part, the check valve preventing a backflow of air from the suction line or the suction space into the socket; an outlet line;
a second check valve positioned in the outlet line.

2. The prosthetic knee joint as claimed in claim 1, wherein the vacuum pump is designed such that the vacuum is generated during flexion of the prosthetic knee joint and an expulsion occurs during extension of the prosthetic knee joint.

3. The prosthetic knee joint as claimed in claim 1, wherein the suction piston is an oscillating piston or linear piston.

4. The prosthetic knee joint as claimed in claim 3, wherein the prosthetic knee joint is a monocentric or polycentric joint.

5. The prosthetic knee joint as claimed in claim 1, wherein the force-transferring device is arranged to convert a pivot movement between the upper part and the lower part into a linear movement of the suction piston.

6. The prosthetic knee joint as claimed in claim 5, wherein the force-transferring device is designed as a lever or a toothed wheel.

7. The prosthetic knee joint as claimed in claim 1, wherein a noise damper is arranged in the outlet line.

8. A prosthetic knee joint, comprising:
an upper part configured for attachment of the prosthetic knee joint to a thigh socket, the upper part having a solid construction;
a lower part pivotally mounted to the upper part and configured for attachment of the prosthetic knee joint to a device below the knee joint;
a vacuum pump integrated into the upper part, the vacuum pump including a piston;
at least one piston bore formed in the upper part of the prosthetic knee joint, the piston being positioned in the at least one piston bore and operable to generate a vacuum upon relative pivotal movement between the upper and lower parts of the prosthetic knee joint to provide the vacuum to the thigh socket;
wherein a force-transferring device is arranged between the upper part and the lower part to transfer the relative movement to the vacuum pump.

9. The prosthetic knee joint as claimed in claim 8, wherein the vacuum pump is designed such that the vacuum is generated during flexion and an expulsion occurs during extension.

10. The prosthetic knee joint as claimed in claim 8, wherein the piston is an oscillating piston or linear piston.

11. The prosthetic knee joint as claimed in claim 10, wherein the prosthetic knee joint is a monocentric or polycentric joint.

12. The prosthetic knee joint as claimed in claim 8, wherein the force-transferring device comprises a lever or a toothed wheel.

13. The prosthetic knee joint as claimed in claim 8, wherein a check valve operates to prevent a backflow of air into a suction line or a suction space of the vacuum pump.

14. The prosthetic knee joint as claimed in claim 8, wherein the vacuum pump includes an outlet line with a check valve.

15. A prosthetic knee joint, comprising:
an upper part having an upper connector configured to connect the prosthetic knee joint to a proximal prosthetic member, the upper part having a solid construction;
a lower part pivotally mounted to the upper part and having a lower connector configured to connect the prosthetic knee joint to a distal prosthetic member;
a vacuum pump integrated into the upper part, the vacuum pump including a piston;
at least one piston bore formed in the upper part of the prosthetic knee joint, the piston being positioned in the at least one piston bore and operable to generate a vacuum upon relative pivotal movement between the upper and lower parts of the prosthetic knee joint to provide the vacuum to a socket for holding a residual limb;
wherein a force-transferring device is arranged between the upper part and the lower part to transfer the relative movement to the vacuum pump.

16. The prosthetic knee joint as claimed in claim 15, wherein the vacuum pump is designed such that the vacuum is generated during flexion and an expulsion occurs during extension.

17. The prosthetic knee joint as claimed in claim 15, wherein the piston is an oscillating piston or linear piston and is arranged in the vacuum pump.

* * * * *